United States Patent
Fan (10) Patent No.: US 9,333,210 B2
(45) Date of Patent: May 10, 2016

(54) MEDICINE COMPOSITION CONTAINING VITAMIN D AND METFORMIN

(75) Inventor: Fulin Fan, Guangzhou (CN)

(73) Assignee: GUANGDONG TAIHE MEDICINE SCIENCE & TECHNOLOGY CO., LTD, Guangdong (CN)

(*) Notice: Subject to any disclaimer, the term of this patent is extended or adjusted under 35 U.S.C. 154(b) by 90 days.

(21) Appl. No.: 13/980,019

(22) PCT Filed: Aug. 17, 2011

(86) PCT No.: PCT/CN2011/078514
§ 371 (c)(1),
(2), (4) Date: Aug. 12, 2013

(87) PCT Pub. No.: WO2012/106947
PCT Pub. Date: Aug. 16, 2012

(65) Prior Publication Data
US 2014/0031322 A1    Jan. 30, 2014

(30) Foreign Application Priority Data
Feb. 11, 2011   (CN) .......................... 2011 1 0036080

(51) Int. Cl.
*A61K 31/59* (2006.01)
*A61K 31/155* (2006.01)
*A61K 31/592* (2006.01)
*A61K 31/593* (2006.01)

(52) U.S. Cl.
CPC .............. *A61K 31/59* (2013.01); *A61K 31/155* (2013.01); *A61K 31/592* (2013.01); *A61K 31/593* (2013.01)

(58) Field of Classification Search
USPC ........................................................ 514/167
See application file for complete search history.

(56) References Cited

U.S. PATENT DOCUMENTS 6,831,102 B2 * 12/2004 Hangeland ..................... 514/532
2009/0163452 A1 * 6/2009 Schwartz ....................... 514/167

OTHER PUBLICATIONS

Kooy Adrian, (AN 2011-P73878 WPIX abstract of WO 2011149337).*
Rashidi et al., Therapeutic effects of vitamin D and calcium in patients with polycystic ovary syndrome. Abstract. Faslnamah-I Pizishki-I Bravar va Nabaravar 7(3).
Rashidi et al., The effects of calcium-vitamin D and metformin on polycystic ovary syndromeapilot study. Taiwan J Obstet Gynecol • Jun. 2009 • vol. 48 • No. 2.
Jorde et al. Supplementation with cholecalciferol does not improve glycaemic control in diabetic subjects with normal serum 25-hydroxyvitamin D levels. Eur J Nutr (2009) 48:349-354.
Diabetes and osteoporosis. PAN Qi, Guo Li-x. ChinaChinese_J_Pract_Internal_Med_Oct_2009.

* cited by examiner

*Primary Examiner* — Sabiha N Qazi
(74) *Attorney, Agent, or Firm* — Adam Warwick Bell; Matthew Rupert Kaser (57) ABSTRACT

A medicine composition contains vitamin D and metformin, wherein vitamin D comprises vitamin D2, vitamin D3, alphacalcidol, calcifediol, calcitriol, and dihydrotachysterol. The composition can be used in the preparation of a medicine for treating and/or preventing a polyp and cancer in large intestine.

10 Claims, 3 Drawing Sheets

MEDICINE COMPOSITION CONTAINING VITAMIN D AND METFORMIN

FIELD OF THE INVENTION

The present invention relates to the pharmaceutical field, and particularly relates to pharmaceutical compositions containing vitamin D or the derivatives thereof and a biguanide drug, as well as the use of said compositions in the prevention and treatment of diseases such as the occurrence, hyperplasia, recurrence of colorectal polyps, colorectal cancer and so on.

BACKGROUND OF THE INVENTION

Colorectal polyps mean an eminence lesion from the mucosal surface protruding into enteric cavity, pedicled or not pedicled. Some of the colorectal polyps are neoplastic polyps, some are non-neoplastic polyps; wherein the neoplastic polyps account for 70-80% of total colorectal polyps, and are closely related to colorectal cancer.

The treatment of colorectal polyps is to remove immediately the polyps after discovery, and the dominant surgical method is through endoscopy. Colorectal polyps in patients are asymptomatic or without obvious symptoms, and thus, clinically, attention is always paid on colorectal cancer, causing the early detection and treatment of colorectal polyps to be often disregarded or even ignored. However, colorectal polyps have multiple malignant tendencies, and are one of the important causes of colorectal cancer. Prevention of colorectal cancer by preventing colorectal polyps is worth exploring. In western developed countries, colonoscopy screening is generally applied on asymptomatic normal people over 50, and early detection and removal of colorectal polyps are proved to be the only way to extend the life by far.

Colorectal cancer is the general term of colon and rectal cancer. Colorectal cancer is colorectal mucosal epithelium malignant lesions resulting from many possible carcinogenic factors such as environmental or genetic factors, with poor prognosis and high mortality rate. Colorectal cancer consists of malignant tumors that originated from colorectal mucosal epithelium, and is one of the most common gastrointestinal cancers. Recent studies suggest that its development path is "normal mucosa—aberrant crypt lesions—colorectal polyps adenoma—adenocarcinoma".

China is a low-incidence area for colorectal cancer in the world, but in recent years, colorectal cancer rate, like lung cancer rate, has shown a rapid upward trend. The causes of colorectal cancer, like those of other malignancies, are not yet clear, and may be related to environmental factors, genetic factors, colorectal adenoma, chronic inflammation of the large intestine, and the like. The first choice for treating colorectal cancer is surgical resection of the tumor, supplemented by radiotherapy, chemotherapy drugs and Chinese medicine treatment.

However, so far, there is no satisfactory therapeutical medicine for colorectal polyps and colorectal cancer; therefore, it is urgently needed in the art to develop new drugs for treating and/or preventing colorectal polyps and colorectal cancer.

SUMMARY OF THE INVENTION

The object of the present invention is to provide a new pharmaceutical composition that can effectively treat and/or prevent of colorectal polyps and colorectal cancer.

Another object of the present invention is to provide the use of said pharmaceutical composition in the treatment and/or prevention of colorectal polyps and colorectal cancer and other diseases.

In the first aspect of the invention, a pharmaceutical composition is provided, comprising:
an active ingredient (a) of Vitamin D;
an active ingredient (b) of metformin or the pharmaceutically acceptable salts thereof; and
(c) a pharmaceutically acceptable carrier.

In another preferred embodiment, the pharmaceutically acceptable salt of metformin is metformin hydrochloride.

In another preferred embodiment, the Vitamin D includes Vitamin D2, Vitamin D3, alfacalcidol, calcifediol (25-hydroxyvitamin D), calcitriol (1α,25-dihydroxyvitamin D), dihydrotachysterol (DHT), or the combinations thereof.

In another preferred embodiment, the ratio (international unit U:mg) of the active ingredient (a) to the active ingredient (b) is 1:100 to 50:1; preferably 1:12 to 15:2; and more preferably 1:4 to 5:2.

Generally, the ratio of the active ingredient (a) to the active ingredient (b), by weight, is 0.00125-0.125 mg of Vitamin D:100-5000 mg of metformin hydrochloride; preferably 0.0075-0.075 mg of Vitamin D:400-3600 mg of metformin hydrochloride; and more preferably 0.0075-0.025 mg of Vitamin D:400-1200 mg of metformin hydrochloride.

In another preferred embodiment, the total amount of the active ingredient (a) and the active ingredient (b) is 1-99 wt %; and more preferably 5-90 wt %.

In another preferred embodiment, the pharmaceutical composition further comprises other pharmaceutically active ingredients, including the active ingredients for treating tumors, such as cis-platin, taxol, or antibody against tumors, and the like.

In another preferred embodiment, the composition is in oral dosage form, including tablets, capsules, film, granules, further including controlled-released form or uncontrolled-release form.

In the second aspect of the invention, use of the pharmaceutical composition according to the first aspect of the invention is provided, for preparing drugs for treating and/or preventing colorectal polyps and colorectal cancer.

In another preferred embodiment, the treating or the preventing includes reducing the number of colorectal aberrant crypt lesions.

In the third aspect of the invention, use of a combination or a mixture consisting of an active ingredient (a) of Vitamin D and an active ingredient (b) of metformin or the pharmaceutically acceptable salts thereof is provided, for treating and/or preventing colorectal polyps and colorectal cancer.

In the forth aspect of the invention, a kit is provided, containing:
(i) a first container which contains an active ingredient (a) of Vitamin D or a drug comprising the active ingredient (a);
(ii) a second container which contains an active ingredient (b) of metformin or the pharmaceutically acceptable salts thereof or a drug comprising the active ingredient (b); and
(iii) an instruction recording an administration of the active ingredient (a) in combination with the active ingredient (b) for treating and/or preventing colorectal polyps and colorectal cancer.

In another preferred embodiment, the drug in the first container and the second container is a single dosage of active ingredient (a) and a single dosage of active ingredient (b).

In another preferred embodiment, the dosage form of the drug is the oral dosage form.

In the fifth aspect of the invention, a method for treating and/or preventing colorectal polyps and colorectal cancer is provided, comprising the following steps: administrating to a mammal in need thereof an active ingredient (a) of Vitamin D and an active ingredient (b) of metformin or the pharmaceutically acceptable salts thereof, or a pharmaceutical composition comprising the active ingredient (a) and the active ingredient (b).

In another preferred embodiment, the administrating includes administrating simultaneously or sequentially. The administrating sequentially includes administrating the active ingredient (a) and (b) sequentially, or administrating the active ingredient (b) and (a) sequentially within 24 hours, preferably, within 12 hours, and more preferably, within 6 hours.

In another preferred embodiment, said mammal includes human.

It should be understood that, in the present invention, the technical features specifically described above and below (such as in the Examples) can be combined with each other, thereby constituting new or preferred technical solutions, which need not be specified herein.

DESCRIPTION OF FIGURES OF THE INVENTION

DETAILED DESCRIPTION OF THE INVENTION

Through comprehensive and intensive research and screening, the inventors surprisingly discovered that two active ingredients—(a) vitamin D or the derivatives thereof and (b) metformin or the pharmaceutically acceptable salts thereof can synergistically and effectively prevent and inhibit the occurrence, hyperplasia, recurrence of colorectal polyps, and colorectal cancer. On this basis, the present invention is completed.

Vitamin D or the Derivatives Thereof

In the compositions of the present invention, one of the most important active ingredients is vitamin D and the derivatives thereof.

Vitamin D and the derivatives thereof (Vitamin D and Analogs) are always considered as vitamin medicaments, mainly for preventing and treating vitamin D deficiency, and also for preventing and treating hypocalcemia, hypophosphatemia, rickets, osteomalacia, infantile tetany etc. High doses of vitamin D can also be used for skin tuberculosis, skin and mucosa lupus erythematosus etc. Vitamin D, mainly including vitamin D2 and vitamin D3, is a steroid derivative with biological activity of cholecalciferol. Vitamin D is the derivatives produced by various pro-Vitamin D upon UV irradiation.

As used herein, the term "vitamin D", includes vitamin D, and also includes the prodrug or derivatives of vitamin D, such as alfacalcidol, calcifediol (25-hydroxy-vitamin D), calcitriol (1α,25-dihydroxy vitamin D), dihydrotachysterol (DHT), etc., that belong to the same family and have the same clinical and medical effects. These derivatives can be converted into vitamin D or the analogue thereof in vivo, which have the same or similar biological activities as vitamin D2 or D3.

In the compound prescription pharmaceutical composition (or the single prescription pharmaceutical composition) of the present invention, the amount of vitamin D is generally 0.0075-0.075 mg (or 300-3000 IU) per tablet (per dose), preferably 0.0075-0.025 mg (300-1000 international units or units) per tablet (per dose).

Metformin or the Pharmaceutically Acceptable Salts Thereof

In the composition of the present invention, another important active ingredient is metformin or the pharmaceutically acceptable salts thereof.

A common pharmaceutically acceptable salt of metformin is metformin hydrochloride. Metformin hydrochloride belongs to oral hypoglycemic agents of biguanide, and has been used in the clinical treatment of type II diabetes for many years.

In the compound prescription pharmaceutical composition (or the single prescription pharmaceutical composition) of the present invention, the amount of metformin or the pharmaceutically acceptable salts thereof usually is 0.3-3.0 g per tablet (per dose), and preferably 1-1.5 g per tablets (per dose).

In the present invention, the ratio (U:mg) of the active ingredient (a) to the active ingredient (b) is generally 1:100 to 50:1; preferably, 1:12 to 15:2; and more preferably, 1:4 to 5:2.

Furthermore, the ratio (by weight) of vitamin D to metformin or the pharmaceutically acceptable salts is generally $1:4.8\times10^5$ to $3:1.6\times10^4$; and more preferably, $1:1.6\times10^5$ to $1:1.6\times10^4$. Preferably, the weight ratio of the active ingredient (a) to (b) is generally 0.00125-0.125 mg of Vitamin D:100-5000 mg of metformin hydrochloride; preferably, 0.0075-0.075 mg of Vitamin D:400-3600 mg of metformin hydrochloride; and more preferably, 0.0075-0.025 mg of vitamin D:400-1200 mg of metformin hydrochloride.

Compound Prescription Pharmaceutical Compositions and Kits

In the present invention, a compound prescription pharmaceutical composition is provided, comprising an active ingredient (a) of vitamin D; an active ingredient (b) of metformin or the pharmaceutically acceptable salts thereof; and (c) a pharmaceutically acceptable carrier.

The dosage forms and preparation methods for the compound prescription pharmaceutical composition of the present invention are not particularly limited, and the composition can be made into various dosage forms such as tablets, capsules, granules, sustained-release agents, injections, and the like by conventional processes in the art. A preferred dosage form is the oral dosage form.

In the invention, a kit for preventing or treating colorectal polyps and colorectal cancer is also provided, comprising:

(i) a first container which contains an active ingredient (a) of Vitamin D or a drug comprising the active ingredient (a);

(ii) a second container which contains an active ingredient (b) of metformin or the pharmaceutically acceptable salts thereof or a drug comprising the active ingredient (b);

(iii) an instruction recording an administration of the active ingredient (a) in combination with the active ingredient (b) for treating and/or preventing colorectal polyps and colorectal cancer.

In another preferred embodiment, the drug is the single prescription formulation comprising active ingredient (a) and the single prescription formulation comprising active ingredient (b).

In another preferred embodiment, the dosage form for the drug is the oral dosage form.

The formulations and kits of the present invention are used for preventing and treating the hyperplasia, relapse, recurrence of colorectal polyps, particularly for reducing the number of colorectal aberrant crypt foci.

The formulations and kits of the present invention are also used for preventing and treating colorectal cancer.

The formulations of the invention may be administrated once or twice a day, or administrated once every other day in a sustained-release manner. Preferably, the formulation is administrated once a day, since it is easy for the patient to take the medicine over a long period, thereby significantly improving the patient's compliance.

For most of the cases, while being administrated, the total daily dose administrated should be generally less than (for few cases, should be equal to or slightly greater than) the common daily dose of each single drug, i.e. for most of the cases, the daily dose of vitamin D should be less than 0.025 mg (or 1000 unit), and the daily dose of metformin or the pharmaceutically acceptable salts thereof should be less than 1200 mg (for a human of 60 kg) per day. Of course, the effective dosage of the active ingredients can be varied according to the administration mode and the severity of the disease to be treated.

Methods of Treatment and Prevention

In the invention, a method for treating and preventing colorectal polyps and/or colorectal cancer by using two active ingredients of the invention or the corresponding drugs is provided, which comprises administrating to the mammal an effective amount of an active ingredient (a) of vitamin D and an active ingredient (b) of metformin or the pharmaceutically acceptable salts thereof, or administrating a pharmaceutical composition comprising the active ingredient (a) and the active ingredient (b).

When the two active ingredients of the present invention are used for the above use, they can be mixed with one or more pharmaceutically acceptable carriers or excipients, such as solvents, diluents, and the like, and can be administrated orally in the following forms: tablets, pills, capsules, dispersible powders, granules or suspensions (containing, for example about 0.05 to 5% suspending agent), syrup (containing, for example about 10 to 50% sugar), and elixirs (containing about 20-50% ethanol); or in the form of sterile injectable solutions or suspensions (containing about 0.05 to 5% suspending agent in an isotonic medium) for parenteral administration. For example, the pharmaceutical preparations may contain about 0.01 to 99% and preferably about 0.1% to 90% (by weight) of the active ingredients mixed with the carriers.

The two active ingredients or pharmaceutical compositions of the present invention may be administrated by conventional routes, including (but not limited to): intramuscular, intraperitoneal, intravenous, subcutaneous, intradermal, oral, or topical administration. Preferred routes of administration include oral administration.

The preferred pharmaceutical compositions are solid compositions for convenient administration, especially the tablets and solid filled or liquid-filled capsules.

Furthermore, the two active ingredients or drugs of the present invention can be used in combination with other drugs for treating cancer (such as cis-platin, paclitaxel, anti-tumor antibodies).

The main advantages of the present invention are:

(a) It discloses the effect of vitamin D in combination with metformin in the prevention of occurrence, hyperplasia, recurrence of colorectal polyps, and colorectal cancer, and provides an use of the combination of vitamin D and metformin in the preparation of the relevant drugs.

(b) Vitamin D and metformin are common drugs, and safe.

(c) The simultaneous administration of vitamins and metformin possesses synergistic inhibition for precancerous lesions of colorectal cancer (ACF) and tumors, and has medically relevant statistical significance, thereby further reducing the dose of drugs.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacture's instructions. Unless indicated otherwise, parts and percentage are calculated by weight.

EXAMPLE 1

The Chemoprevention of Vitamin D3 and Metformin for Colorectal Cancer

1. Purpose of the Experiment

Wistar rats with dimethyl hydrazine-induced colorectal cancer were used as the model to study the chemoprevention by the combined administration of vitamin D3 and metformin hydrochloride for colorectal cancer and the effect on colorectal cancer.

2. Animal and Materials 2.1 Experimental animals: Wistar rats (110), male, SPF grade, weight 80-120 g, purchased from the Experimental Animal Center of Southern Medical University, qualification No: SCXK Guangdong 2006-0015.

2.2 Drugs and reagents: dimethyl hydrazine (1,2-Dimethylhydrazine dihydrochloride, DMH), Tokyo Yan cheng Industrial Co., Ltd., Lot: EZC6C; Vitamin D3 injection solution (Vitamin D), Shanghai General Pharmaceutical Co., Ltd., Lot: 090812; metformin hydrochloride (Metformin Hydrochloride, MF), Zhengzhou Lai Connaught Biological Technology Co., Ltd.; soybean oil, YiHai Kerry food Marketing Ltd., Lot: 20091027; methylene blue, Tianjin Damao Chemical Reagent.

3.1 Grouping and Processing

Experimental animals were randomly divided into 11 groups (each group having 10), including blank control group, model control group, low, medium and high dose groups of vitamin D3, low, medium and high dose groups of metformin, and three groups of different doses of vitamin D3 in combination with metformin. Except for the blank control group, other groups were subcutaneously injected with dimethyl hydrazine once a week respectively for 18 weeks, to induce colorectal cancer model. Dimethylhydrazine was dissolved in sodium chloride injection, and into the solution, 5% NaOH solution was added to adjust pH to 6.5-7.0, thereby obtaining a 20 mg/ml solution. The resulting solution was filtered through 0.22 μm membrane, and prepared extemporaneously.

Vitamin D3 was prepared into 10-100 U/ml solution by using soybean oil, and intragastrically administrated, once a day. Metformin was prepare into 10-100 mg/ml solution, and administrated intragastrically, once a day. The above drugs were administrated from day 0. Dose of each experimental group are shown in Table 1.

All the animals were sacrificed at the end of 18th weeks after administration. Body weights were recorded once a week during the experiment, and the administrated dose was calculated based on the body weight. The animals that died during the experiment were dissected and observed.

TABLE 1 group and dose for Experimental animals

| Group | Number of the Animals | DMH (mg/kg) | Vitamin D (U/kg) | Metformin Hydrochloride (mg/kg) |
|---|---|---|---|---|
| Blank control group | 10 | | | |
| model control group | 10 | 30 | | |
| low dose group of vitamin $D_3$ | 10 | 30 | 30 | |
| medium dose group of vitamin $D_3$ | 10 | 30 | 100 | |
| high dose group of vitamin $D_3$ | 10 | 30 | 300 | |
| low dose group of metformin | 10 | 30 | | 40 |
| medium dose group of metformin | 10 | 30 | | 120 |
| High dose group of metformin | 10 | 30 | | 360 |
| Combination group A | 10 | 30 | 100 | 40 |
| Combination group B | 10 | 30 | 30 | 120 |
| Combination group C | 10 | 30 | 100 | 120 |

3.2 Results 3.2.1 The animals were observed daily to record the general conditions, such as mental activity, food-taking, feces, hair, and the like.

3.2.2 The large intestine was separated immediately after the animals were sacrificed, the contents of the intestine were washed away with saline, and colorectal tumors were visually observed to calculate the number of tumors. The entire colon was paved between two layers of filter paper, placed in 10% neutral formalin and fixed for 24-48 h. The fixed large intestine tissue was put into 0.2% methylene blue and stained for 10 s. The aberrant crypt foci (ACF) of the whole large intestine were immediately observed under an optical microscope, and the number of the aberrant crypt in foci was counted respectively as one, two, three and four as well as greater than four.

3.2.3 The data were processed by using Excel 2003 software for statistical analysis, and the obtained data were represented by mean±standard deviation (mean±SD). P<0.05 means that there is statistically significant difference between two groups.

4 Results 4.1 General Situation

During the experiment, none of the rats was dead. Other situations, such as mental activity, food-taking, feces, hair, and the like were not significantly different. At the $18^{th}$ week, the weight gain of rats in the blank control group was higher than that in the groups injected with dimethylhydrazine, while the weight gain of each metformin-administrated group was lower. Body weights of rats in each group were shown in Table 2.

Generally, for the rats in each group, obvious abnormal lesions in the organs, such as peritoneum, liver, spleen and the like, have not been observed.

TABLE 2 the variation in body weights for the animals in each group after 18 weeks

| Group | Week 0 | Week 18 | Weight gain |
|---|---|---|---|
| Blank control group | 101.3 ± 3.6 | | 272.6% |
| model control group | 99.0 ± 5.4 | | 197.4% |
| low dose group of vitamin D3 | 100.3 ± 4.1 | 377.5 ± 27.5 | 227.7% |
| medium dose group of vitamin D3 | 102.9 ± 5.8 | 294.3 ± 22.1 | 235.7% |
| high dose group of vitamin D3 | 101.5 ± 5.2 | 328.8 ± 23.6 | 225.7% |
| low dose group of metformin | 102.3 ± 6.4 | 345.5 ± 25.9 | 198.9% |
| medium dose group of metformin | 102.1 ± 6.6 | 330.6 ± 24.6 | 197.5% |
| high dose group of metformin | 102.7 ± 5.5 | 305.7 ± 33.9 | 168.7% |
| Combination group A | 99.4 ± 4.0 | 303.7 ± 30.1 | 178.4% |
| Combination group B | 101.6 ± 4.6 | 276.0 ± 12.3 | 187.6% |
| Combination group C | 102.8 ± 4.2 | 276.8 ± 25.8 | 187.1% |

4.2 Results of Aberrant Crypt Foci (ACF)

At the end of week 18, ACF was not found in the blank control group, while appearing in all of the other groups. Compared with the control group, the number of various ACF containing different crypt numbers was reduced, and the total number of ACF was significantly reduced. In the Vitamin $D_3$ group, the inhibitory effect on ACF increased with the increase of dose. The same trend can also be observed in the metformin group.

Surprisingly, for the combination group of vitamin $D_3$ and metformin, a synergistic effect can be observed in each group. The inhibitory effect of two groups containing medium dose of vitamin $D_3$ and low dose of metformin or low dose of vitamin $D_3$ and medium dose of metformin on ACF was better than the middle dose group of vitamin $D_3$ or metformin, and close to the high dose group. The effect of medium dose group of vitamin D3 in combination with metformin was the best in each experimental groups, and significantly higher than that of the high dose group of vitamin D3 or metformin alone (P<0.01).

Figure 1:
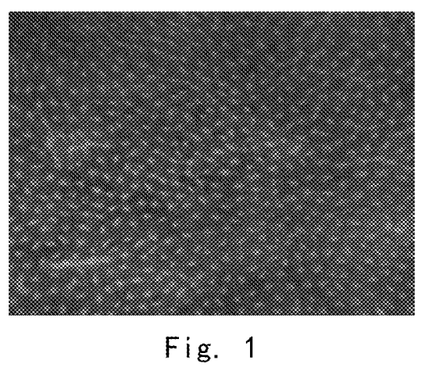
FIG. 1 shows the normal Crypt.
Figure 2:
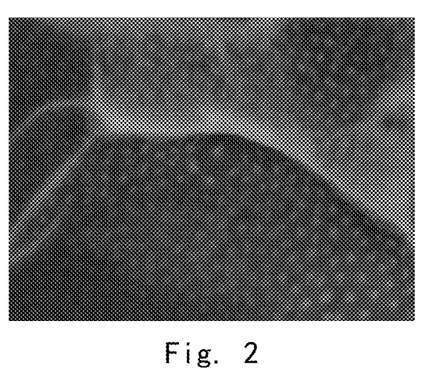
FIG. 2 shows the aberrant crypt foci ACF (AC=1).
Figure 3:
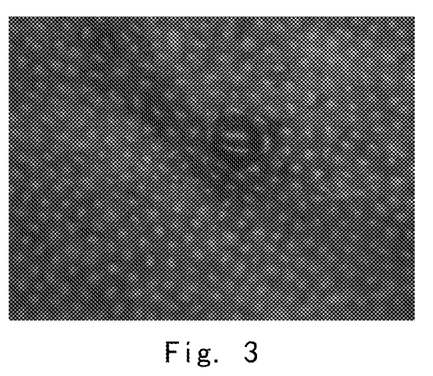
FIG. 3 shows the aberrant Crypt foci ACF (AC=2).
Figure 4:
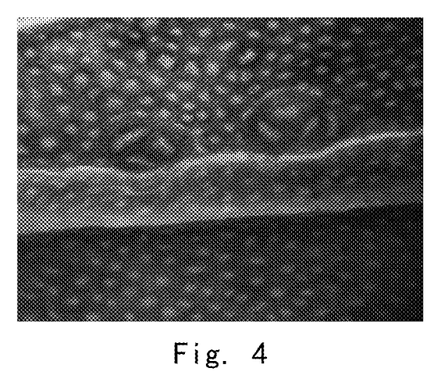
FIG. 4 shows the aberrant Crypt foci ACF (AC=3).
Figure 5:
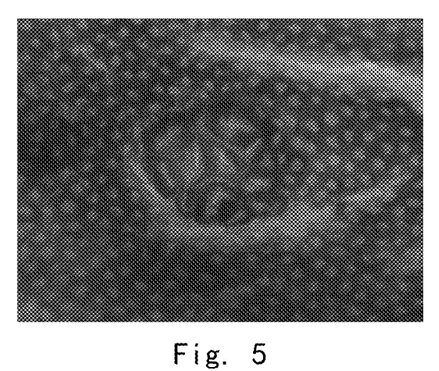
FIG. 5 shows the aberrant Crypt foci ACF (AC>4).
Figure 6:
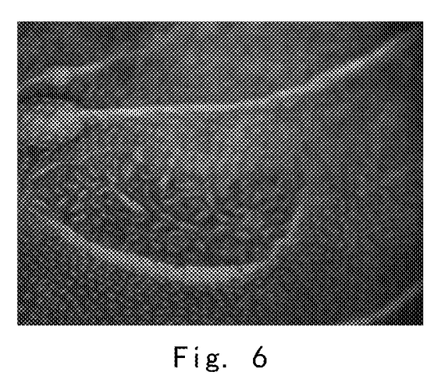
FIG. 6 shows mucosal hyperplasia.
Figure 7:
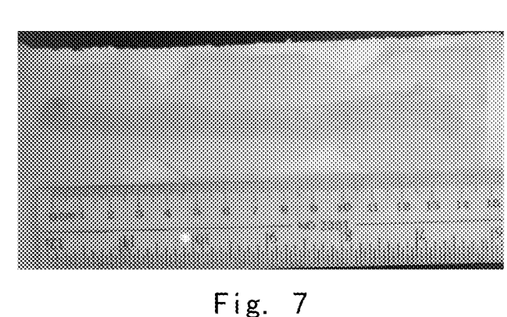
FIG. 7 shows the large intestine mucosa (normal).
Figure 8:
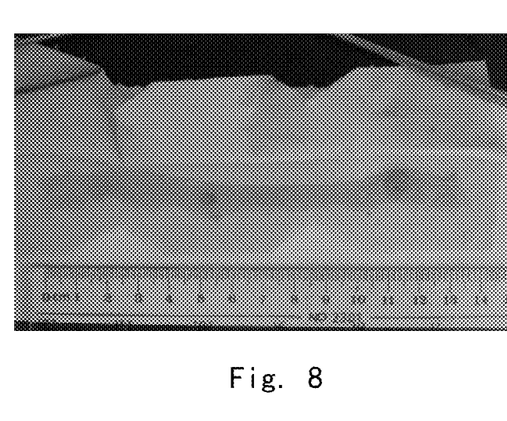
FIG. 8 shows the large intestine mucosa (tumorigenesis).
Figure 9:
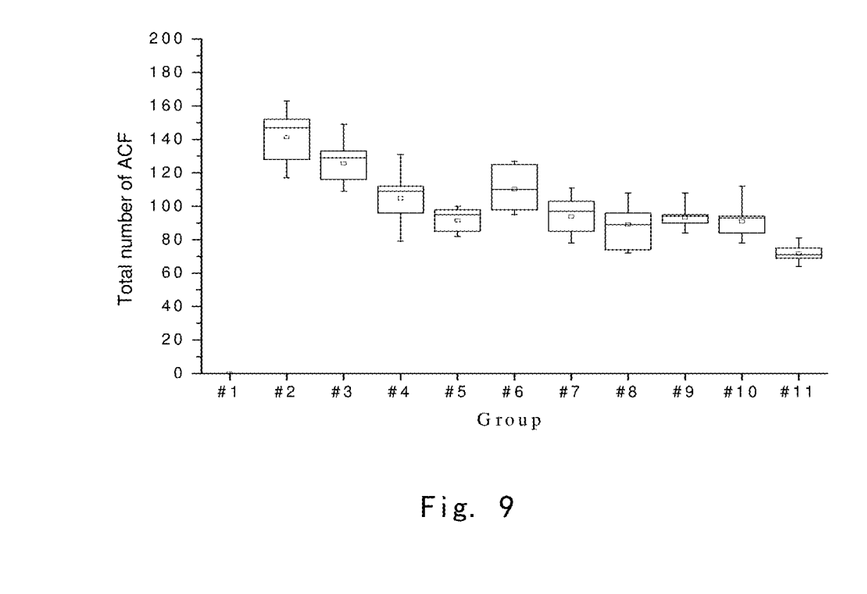
FIG. 9 shows the total number of ACF in each experimental group. Wherein, group #1 to #11 are blank control group, model control group, low dose group of vitamin D3, medium dose group of vitamin D3, high dose group of vitamin D3, low dose group of metformin, medium dose group of metformin, high dose group of metformin, combined administration group A, combined administration group B, combined administration group C, respectively (see table 3).

Experimental results were shown in FIG. 1-8 and Table 3 as well as FIG. 9.

TABLE 3 the change in ACF number in each group

| Groups | The total number of ACF | ACF | | | |
|---|---|---|---|---|---|
| | | AC = 1 | AC = 2 | AC = 3 | AC ≥ 4 |
| Blank control group | 0.0 ± 0.0 | 0.0 ± 0.0 | 0.0 ± 0.0 | 0.0 ± 0.0 | 0.0 ± 0.0 |
| model control group | 141.3 ± 15.2 | 92.6 ± 10.7 | 17.3 ± 6.4 | 9.9 ± 3.0 | 21.5 ± 5.3 |
| low dose group of vitamin D3 | 125.6 ± 12.1[#] | 80.5 ± 7.6 | 16.1 ± 5.7 | 9.0 ± 2.3 | 20.0 ± 4.1 |
| medium dose group of vitamin D3 | 104.7 ± 14.3[##] | 67.9 ± 11.8 | 15.9 ± 5.7 | 4.8 ± 3.1 | 16.1 ± 2.9 |

TABLE 3-continued the change in ACF number in each group

| Groups | The total number of ACF | ACF AC = 1 | AC = 2 | AC = 3 | AC ≥ 4 |
|---|---|---|---|---|---|
| High dose group of vitamin D3 | 91.5 ± 7.2## | 61.8 ± 11.1 | 14.9 ± 5.9 | 5.0 ± 1.6 | 9.8 ± 2.2 |
| low dose group of metformin | 110.3 ± 13.0## | 70.4 ± 10.6 | 16.7 ± 3.6 | 6.7 ± 1.7 | 16.5 ± 2.1 |
| medium dose group of metformin | 93.8 ± 11.7## | 57.0 ± 10.7 | 16.6 ± 1.8 | 5.4 ± 1.6 | 14.8 ± 3.0 |
| High dose group of metformin | 89.0 ± 12.7## | 61.5 ± 8.1 | 13.8 ± 3.4 | 4.0 ± 1.2 | 9.7 ± 3.2 |
| Combination group A | 93.4 ± 6.9## | 61.6 ± 5.9 | 15.3 ± 2.7 | 6.5 ± 0.7 | 10.0 ± 1.6 |
| Combination group B | 90.9 ± 9.7## | 59.8 ± 4.7 | 14.7 ± 3.1 | 6.2 ± 0.8 | 10.2 ± 3.2 |
| Combination group C | 71.7 ± 5.0## | 46.3 ± 3.9 | 12.1 ± 1.7 | 5.6 ± 0.7 | 7.7 ± 1.7 |

PS: compared with modal control group,
$p < 0.05$,
$p < 0.01$
"AC" represents aberrant crypt.

4.3 Tumorigenesis and Tumor Inhibition Rate

At the end of week 18, in the blank control group, tumor was not found in any rat, and was found in all of the rats in modal control group, with the average number of tumors being 2.8/rat.

Compared with the model control group, the number of tumors decreased in each treatment group. The inhibition rate for tumor increased with the increase of dose in vitamin $D_3$ group. Compared with the model control group, the number of tumors in medium dose group and high dose group was significantly reduced (P<0.01). The number of tumors in metformin group was also reduced with the increase of dose.

For each group of Vitamin $D_3$ in combination with metformin, the numbers of tumors in the two groups containing medium dose of vitamin $D_3$ and low dose of metformin or low dose of vitamin $D_3$ and medium dose of metformin were close to those in the high dose group merely containing vitamin $D_3$ or metformin; the inhibition rate of tumor in the middle dose combination group was the highest, and the number of tumors was lower than that in the high dose group merely containing vitamin $D_3$ or metformin (P<0.01). It is suggested that there is a synergistic effect of metformin in combination with vitamin $D_3$.

TABLE 4 tumorigenesis in colorectal tumor

| Groups | Number of animals | Number of Animals with tumor | Mean number of tumors | Inhibition rate(%) |
|---|---|---|---|---|
| Blank control group | 10 | 10 | 0.0 ± 0.0 | — |
| model control group | 10 | 10 | 2.8 ± 0.8 | — |
| low dose group of vitamin D3 | 10 | 10 | 2.3 ± 0.5 | 17.9 |
| medium dose group of vitamin D3 | 10 | 10 | 1.7 ± 0.7## | 39.3 |
| high dose group of vitamin D3 | 10 | 8 | 1.4 ± 0.8## | 50.0 |
| low dose group of metformin | 10 | 10 | 2.0 ± 0.7# | 28.6 |
| medium dose group of metformin | 10 | 10 | 1.8 ± 0.4## | 35.7 |
| high dose group of metformin | 10 | 10 | 1.6 ± 0.5## | 42.9 |
| Combination group A | 10 | 10 | 1.5 ± 0.5## | 46.4 |
| Combination group B | 10 | 10 | 1.6 ± 0.5## | 42.9 |
| Combination group C | 10 | 7 | 0.9 ± 0.7## | 67.9 |

Ps: compared with the modal control group,
$p < 0.05$,
$p < 0.01$

5. Discussion

Colorectal cancer is a common malignancy, and in recent years, the incidence in our country rose rapidly. The prognosis for this disease is poor, so that chemoprevention for colorectal cancer receives attention. Dimethylhydrazine (DMH) is the animal-specific intestinal tumors inducing agent, especially for colon tumors. Currently, the dimethylhydrazine-induced colon cancer model has been widely used in drug screening for preventing and treating colorectal cancer. Since Bird proposed the concept of aberrant crypt foci (ACF), domestic and abroad scholars recognized ACF as precancerous lesions of colon cancer, and the number of ACF was significantly positively correlated with incidence of tumors.

Vitamin D and metformin are common drugs, and have been used clinically for many years. They are used in vitamin supplements and the treatment of type II diabetes respectively, and are highly safe drugs.

The present invention investigates the preventive effects of high, medium and low doses of vitamin D and metformin on colorectal cancer. Particularly, the oral administration of vitamin D in combination with metformin has been studied, and whether the combination of two drugs will produce synergistic effects has been observed. The results showed that, rats treated by DMH have different levels of ACF formation, and the appearance of tumor has also been observed. Vitamin D or metformin alone can reduce the number of ACF and tumors, and the reduction is more significant as the increase of dose. The effect produced by a medium dose of vitamin D in combination with a low dose of metformin or a low dose of vitamin D in combination with a medium dose of metformin is better than the effect produced by the medium dose of either drug alone and close to the effect produced by the high dose of either drug alone. The effect produced by the medium dose of the two drugs in combination is better than that produced the high dose of either drug alone.

The combination of Vitamin D and metformin showed significant synergistic effect, and can be used as a drug candidate for the chemoprevention and treatment of colorectal cancer.

EXAMPLE 2-6

Compound Pharmaceutical Composition of Vitamin D and Metformin

Compound capsules or sugar-coated tablets were prepared according to the formula in table 1 by the conventional method in pharmaceutical industrial.

| example | The content of Vitamin D (mg/capsule or tablet) | The content of metformin hydrochloride (mg/capsule or tablet) |
|---|---|---|
| 2 | 0.0075 | 400 |
| 3 | 0.0075 | 1200 |
| 4 | 0.025 | 400 |
| 5 | 0.025 | 1200 |
| 6 | 0.025 | 2500 |

Since the content of Vitamin D is smaller, during the preparation, vitamin D was blended with suitable amount of excipients, such as active cellulose and the like, firstly, diluted to a certain weight, and then blended with metformin hydrochloride to form tablets or capsules.

The above compound capsules or sugar-coated tablets may be taken once or twice a day, and 1-2 tablets (or capsules) for one time.

EXAMPLE 7

Kit Comprising Vitamin D and Metformin

A kit was prepared, comprising
(i) a first container which contains Vitamin D tablets (0.025 mg/tablet), 10 tablets;
(ii) a second container which contains metformin hydrochloride tablets (1200 mg/tablet);
(iii) an instruction recording an administration of vitamin D in combination with metformin hydrochloride for treating and/or preventing colorectal polyps and colorectal cancer.

EXAMPLE 8

The Synergistic Effect of Vitamin D Analogues and Metformin

Example 1 was repeated, however, the difference is that vitamin $D_3$ was replaced by calcifediol (25-hydroxy vitamin D). Furthermore, there are 8 animals in each group. Only the number of aberrant crypt foci (ACF) was observed during the experiment.

The results showed that, in each group, 25-hydroxy vitamin D in combination with metformin (three groups: 100 U/kg 25-hydroxyvitamin D+40 mg/kg metformin hydrochloride; 30 U/kg 25-hydroxyvitamin D+120 mg/kg metformin hydrochloride; as well as 100 U/kg 25-hydroxyvitamin D+120 mg/kg metformin hydrochloride) also showed a synergistic effect. Wherein, in the two groups containing medium dose of vitamin $D_3$ and low dose of metformin or low dose of vitamin $D_3$ and medium dose of metformin, the inhibition on ACF is better compared with the middle dose group of 25-hydroxy vitamin D (100 U/kg 25-hydroxy vitamin D) or the middle dose group of metformin (+40 mg/kg metformin hydrochloride), and is close to the high dose group of 25-hydroxyvitamin D.

EXAMPLE 9

Inhibition and Treatment on Colorectal Cancer

Example 1 was repeated, except that: The experimental animals were randomly divided into 11 groups, with 8 in each group. Except for the blank control group, other groups were subcutaneously injected of dimethylhydrazine once a week for 18 weeks to induce colorectal cancer model. Vitamin $D_3$ was prepared into 10-100 U/ml solution by using soybean oil, and intragastrically administrated, once a day. Metformin was prepare into 10-100 mg/ml solution, and administrated orally, once a day. The above drugs were administrated from day 15 (after two weeks). During the experiments, tumorigenesis and inhibition rate were observed.

At the end of the week 18, in the blank control group, no tumors were found in any rat, and in the model control group, all of the rats had tumors, with the average number of tumors being 3.1/rat.

Compared with the model group, the tumor number was reduced in each treatment group. The inhibition rate for tumor increased with the increased of dose in vitamin $D_3$ group. Compared with the model control group, the tumor number in the medium dose group and the high dose group was significantly reduced (P<0.01). The number of tumors was also reduced with the increase of dose in the metformin groups.

In each group of vitamin $D_3$ in combination with metformin, the tumor numbers in the two groups containing medium dose of vitamin $D_3$ and low dose of metformin or low dose of vitamin $D_3$ and medium dose of metformin were close to those in the high dose group merely containing vitamin $D_3$ or metformin; the inhibition rate of tumor in the middle dose combination group was the highest, and the number of tumors was lower than that in the high dose group merely containing vitamin $D_3$ or metformin (P<0.01). It is suggested that there is a synergistic effect of vitamin $D_3$ in combination with metformin for inhibiting and treating colorectal cancer.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

What is claimed:

1. A pharmaceutical composition for treating and/or preventing colonic polyps or colorectal cancer, consisting of a synergistic combination of (a):
   vitamin D3;
   and (b) metformin or a pharmaceutically acceptable salt thereof; and
   (c) a pharmaceutical acceptable carrier; wherein the ratio (International Unit:mg) of (a) to (b) is between 1:12 and 15:2.

2. The pharmaceutical composition according to claim 1, wherein the pharmaceutically acceptable salt of metformin is metformin hydrochloride.

3. The pharmaceutical composition according to claim 1, wherein the ratio (International Unit:mg) of (a) to (b) is 1:4, 5:6 or 5:2.

4. The pharmaceutical composition according to claim 1, wherein the ratio (U:mg) of (a) to (b) is 1:4 to 5:2.

5. The pharmaceutical composition according to claim 1, wherein the total amount of (a) and (b) is 1-99 wt % of the composition.

6. The pharmaceutical composition according to claim 1, wherein the composition is in oral dosage form.

7. A method for treating and/or preventing colorectal polyps and colorectal cancer, comprising administrating to a mammal in need thereof a pharmaceutical composition according to claim 1.

8. The method according to claim 7, wherein the pharmaceutical composition is administrated once or twice a day, or administrated once every other day in a sustained-release manner.

9. The method according to claim 7, wherein the pharmaceutical composition is administrated by oral administration.

10. The method according to claim 7, where the ratio (U:mg) of active ingredient (a) to active ingredient (b) is 1:4 to 5:2.

* * * * *